United States Patent [19]

Coury et al.

[11] Patent Number: 5,278,200
[45] Date of Patent: Jan. 11, 1994

[54] THROMBORESISTANT MATERIAL AND ARTICLES

[75] Inventors: Arthur J. Coury, St. Paul; James R. Keogh, Maplewood; Christopher M. Hobot, Tonka Bay; Warren W. Howland, Brooklyn Center, all of Minn.

[73] Assignee: Medtronic, Inc., Minneapolis, Minn.

[21] Appl. No.: 968,796

[22] Filed: Oct. 30, 1992

[51] Int. Cl.$^5$ ............................................. A01N 1/00
[52] U.S. Cl. .................................. 523/112; 523/105; 604/266
[58] Field of Search ................ 523/105, 112; 604/266; 424/423

[56] References Cited

U.S. PATENT DOCUMENTS

| | | | |
|---|---|---|---|
| 3,826,678 | 7/1974 | Hoffman | 117/81 |
| 4,442,133 | 4/1984 | Greco | 427/2 |
| 4,612,337 | 9/1986 | Fox, Jr. | 523/113 |
| 4,829,098 | 5/1989 | Hoffman | 522/5 |
| 4,895,566 | 1/1990 | Lee | 604/266 |
| 5,004,461 | 4/1991 | Wilson | 604/265 |

OTHER PUBLICATIONS

"Polymer Matrix Based Controlled Adventitial Delivery of Anti-Proliferative Agents and Regulation of the Vascular Response to Injury" by Frazer R. Edelman et al.

"Reactive Site and Mechanism of Graft Copolymerization Onto Poly(ether urethane) with Ceric Ion as Initiator", by Z. Feng et al. in Macromolecules, 18:2105-2109 (1985).

"Synthetic Hydrogels for Biomedical Applications" by B. Ratner and A. Hoffman in Hydrogels For Medical and Related Applications: 1-35 (1976).

"Modification of Polymer Surfaces by Photoinduced Graft Copolymerization" by B. Ranby et al. American Chemical Society, ACS Symposium Series No. 364, (1988).

"Cell Behavior on Polymer Surfaces Grafted with Non-Ionic and Ionic Monomers", by Akio Kishida et al., Biomaterials, 1991, vol. 12, Oct.

"Anticoagulation Activity of the Modified Polyvinyl Alcohol", by Heung-Jae et al. Polymer Journal, vol. 22, No. 4, pp. 347-354 (1990).

"Photoinitiated Graft Copolymerization of HEMA onto Cotton Cellulose", by S. R. Shukla et al., Journal of Applied Polymer Science, vol. 42, 2163-2168 (1991).

"Surface Modification of Polymers V. Biomaterial Applications", by Klas Allmer, et al, Journal of Polymer Science: Part A: Polymer Chemistry, vol. 28, 173-183 (1990).

"Surface Modification of Polymers, II, Grafting with Glycidyl Acrylates and the Reactions of the Grafted Surfaces with Amines", by Klas Allmer, et al. Journal of Polymer Science; Part A; Polymer Chemistry, vol. 27, 1641-1652 (1989).

"Surface Modification of Polymers, I. Vapour Phase Photografting with Acrylic Acid", by K. Allmer et al. Journal of Polymer Science:Part A: Polymer Chemistry, vol. 26, 2099-2111, (1988).

"Surface Modification of Silicone for Tissue Adhesion", by T. Okda et al., Biomaterials and Clinical Applications, Amsterdam, 1987, p. 465.

Primary Examiner—Paul R. Michl
Assistant Examiner—LaVonda DeWitt
Attorney, Agent, or Firm—Daniel W. Latham; Harold R. Patton

[57] ABSTRACT

Biocompatible heparin-like material and surfaces thereof are made by co-polymerization of acrylic acid (AA) and 2-acrylamido-2-methyl propane sulfonic acid (AMPS) and attaching the copolymer to a suitable substrate or blending the copolymer into a suitable substrate. The material produced also possesses surface slip-properties and some decreased bacterial and platelet adherence.

18 Claims, 1 Drawing Sheet

THROMBORESISTANT MATERIAL AND ARTICLES

BACKGROUND OF THE INVENTION

For over forty years a number of medical devices which contact the blood or blood product of living persons or animals have been developed, manufactured and used clinically. A partial list of such articles would include pacemakers, arterial grafts, heart valves, artificial hearts, heart pumps, hip protheses, heart lung machines, catheters and kidney dialysis equipment.

A major problem with such articles is that their working surfaces, (i.e., surfaces which contact blood or blood products), are foreign to blood and blood products and tend to initiate, among other things, red cell destruction and coagulation of blood to form clots (thrombogenesis).

Normal intact endothelium is nonthrombogenic due partly to the synthesis of heparan sulfate. Heparan sulfate tends to remain bound to the surface of endothelial cells accelerating the inactivation of thrombin, the enzyme responsible for the polymerization of fibrinogen to fibrin in clot formation, by ATIII. Heparan sulfate is a very powerful anticoagulant in the natural vasculature. Consequently, it has been of great interest to physicians and the medical industry to devise blood-contacting polymeric surfaces that possess characteristics of heparan sulfate, specifically by coating surfaces with heparin. For example, in U.S. Pat. No. 3,826,678 to Hoffman et al., biologically active molecules are chemically bonded to polymers and copolymers which previously have been radiation-grafted to inert polymeric substrates such as a polyurethane and polyethylene. The grafted polymer is preferably a hydrophilic hydrogel e.g., hydroxyethyl methacrylate (HEMA) and may include heparin bonded to the hydrogel.

The thromboresistant or anticoagulation activity of heparin is believed to be due to the high concentration of anionic groups i.e., sulfonate ($SO_3-$) and carboxylic groups ($COO-$). It is further believed that a material or a surface containing appropriate amounts of sulfonate and carboxylic groups will demonstrate heparin-like activity. i.e. be a heparinoid material. In fact, Chun et al "Anticoagulation Activity of the Modified Poly(vinyl alcohol)" *Polymer Journal* 22(4):347-354. (1990) demonstrated an anticoagulant activity of a blend of 60 wt % sulfonate poly(vinyl alcohol) (PVA) and 40 wt% carboxymethylated PVA.

BRIEF DESCRIPTION OF THE INVENTION

We have discovered a heparinoid material comprised of a copolymer of acrylic acid (AA) and 2-acrylamido-2-methyl propane sulfonic acid (AMPS). The heparinoid material of the present invention may be provided by the generation of free radicals on a material surface and the copolymerization of certain specific vinyl monomers containing sulfonate and carboxylic groups directly to that surface and to the copolymer formed per se. Alternatively, the AMPS/AA copolymer can be prepolymerized in the desired composition and either coated onto a material surface or blended with another polymer to make a material surface with thromboresistance and slip properties. Copolymerization provides a method of controlling the composition of the grafted copolymer by varying the relative amounts of the monomers.

The AMPS/AA copolymer can be engineered stoichiometrically to produce surfaces containing desired predetermined amounts of sulfonate and carboxylic groups. For example, acrylic acid (AA) and 2-acrylamido-2-methyl propane sulfonic acid (AMPS) can be graft polymerized onto poly(ether urethane) and/or other hydrophobic polymeric substrates (e.g. polyethylene or silicone) with CeIV ion. The mechanism of CeIV ion grafting has been reported and is well known.

A heparinoid model based on the graft copolymerization of AA and AMPS is shown below.

Polymeric Hydrophobic Substrate:

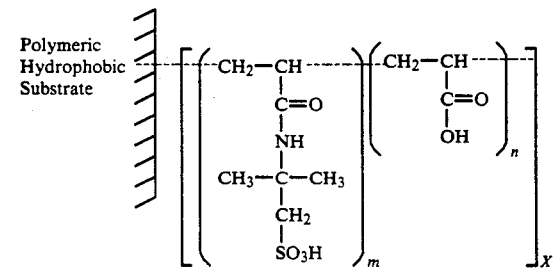

where m is the number of AMPS monomer units
where n is the number of AA monomer units
where x is the number of AMPS/AA block units In one embodiment of the invention, the relative amounts of AA and AMPS provide a heparinoid comparable to the antithrombogenic binding sequence of heparin; approximately 7 moles, $SO_3-$ to 2 moles $COO-$.

The substrate of a working surface of an article intended for blood or blood product contact may be comprised of a biologically inert polymeric material, which may be any of the known implantable type materials including polyethylene, silicone and polyurethane, the latter being the most preferred. According to the invention, a hydrophilic graft copolymer of AA/AMPS is covalently bonded by graft copolymerization to the substrate. Such graft polymers provide thromboresistant slip coatings.

DETAILED DESCRIPTION OF THE INVENTION

Figure 1:
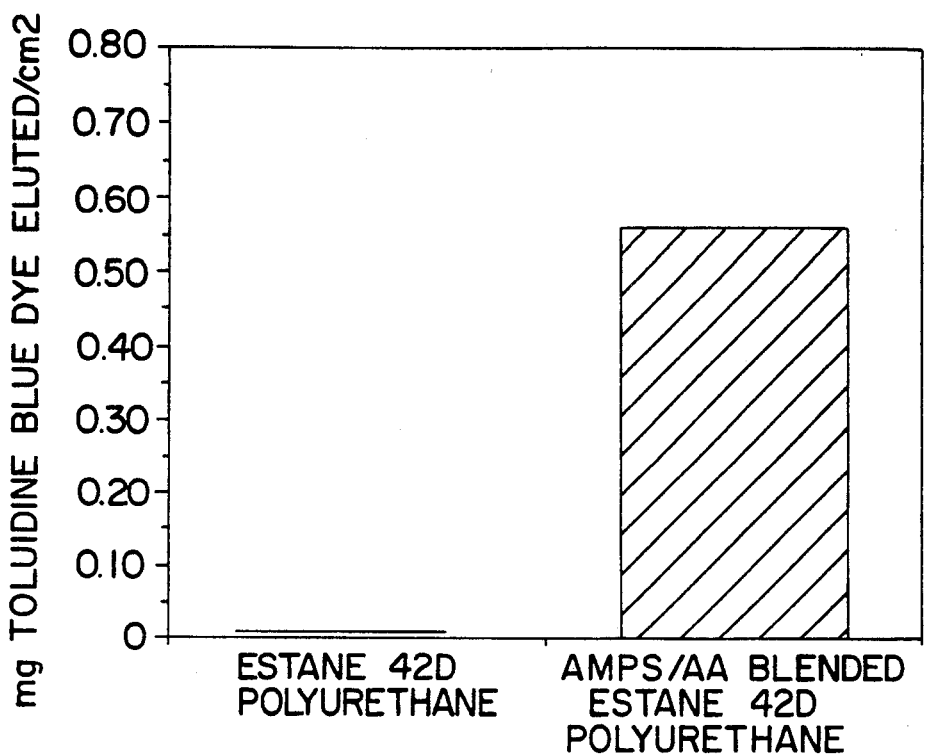
FIG. 1 is a graph comparing the presence of surface sulfonic acid groups and carboxylic acid groups for a polyurethane substrate without an incorporated AMPS/AA copolymer with a polyurethane substrate having an incorporated AMPS/AA copolymer.

The kinds of articles contemplated by this invention may be provided by solid substrates. Preferably, the solid substrates are polymeric substrates selected from the group of materials shown in Table 1. The invention is not limited to these substrates only which are included here by way of example.

TABLE 1

Polyamides

TABLE 1-continued

Polycarbonates
Polyethers
Polyesters
Polyolefins
Polystyrene
Polyurethane
Polyvinyl chlorides
Silicones
Polyethylenes
Polypropylenes
Polyisoprenes
Polytetrafluorethylenes Polyurethane is a preferred polymeric substrate.

The copolymer to be used originates with copolymerizing monomers which are acrylic acid (AA) and 2-acrylamido-2-methyl propane sulfonic acid (AMPS) or their acid salts. Such monomers create a hydrophilic copolymer (AA/AMPS) which can be applied as a coating, either by graft polymerization or dip-coating on the substrate surface and can also be blended with polymeric substrate materials to alter the properties of the polymeric substrate material. The hydrophilic AMPS/AA copolymer minimizes protein interactions and also provides slip properties to the surface. The monomers contain vinyl groups. These groups are necessary for free radical polymerization to occur. They also contain sulfonate and carboxylic groups to simulate heparin's chemical structure. A hydrophilic coating of acrylamide (AAm) and AMPS could also be prepared. After grafting, AAm can be readily hydrolyzed to AA. The resultant grafted copolymer will include AA and AMPS.

Specifically, a number of copolymers have been used according to this invention in which the relative amounts of AA and AMPS have varied.

While ceric ion initiation (CeIV) is presently most preferred as the technique to be used to graft monomers to substrate surfaces, other grafting techniques are well known and may be used in appropriate situations. For example, corona discharge, UV irradiation and ionizing radiation ($^{60}$Co, X-rays, high energy electrons, plasma gas discharge) are known for this purpose. These grafting techniques are examples of how to form free radicals on a polymer substrate working surface. The free radicals formed thereon initiate the grafting of vinyl ($CH_2=CH-R$) type monomers.

The detailed discussion below mentions examples in which treatment is on films as the polymeric substrate surface. However, it is not intended that this invention be so limited. The heparinoid of this invention may be similarly bound to other substrate surfaces, i.e., surfaces of articles intended to contact blood or blood products, of articles of any shape or form including tubular, sheet, rod and articles of proper shape and construction for use in artificial organs, blood handling equipment or bodily implants of any kind and to any encapsulant means therefor.

Normal intact endothelium is nonthrombogenic due partly to the synthesis of heparan sulfate. Heparan sulfate tends to remain bound to the surface of endothelial cells, accelerating the inactivation of thrombin, the enzyme responsible for the polymerization of fibrinogen to fibrin in clot formation, by antithrombin III (ATIII). Heparan sulfate is a very powerful anticoagulant in the natural vasculature. Heparin is a strongly acidic glycosaminoglycan. It has a high content of N- and O sulfate groups and carboxylic groups. Heparin is structurally similar to heparan sulfate although it is more sulfated. The anticoagulant activity of heparin is directly dependent on its molecular size and electric charge, thus increasing the molecular weight and/or the amount of sulfonation will increase the anticoagulant activity. Therefore, it is felt a highly sulfonated and carboxylated polymer surface may stimulate the inhibition of thrombin by ATIII.

The copolymer material and coating of this invention is aimed at producing a surface that will decrease the nonspecific adsorption of various proteins due to its hydrophilicity and provide a highly sulfonated and carboxylated surface that will preferentially asorb ATIII.

Much of the work effort relative to this invention went into developing a general surface modification technique for polyurethanes, however, the technique may be used for other material surfaces with a few modifications. The preferred technique developed is based on the generation of free radicals on a polyurethane surface with CeIV ion and the graft copolymerization of AAm or AA and AMPS monomers directly to that surface in predetermined relative amounts. If AAm monomer is used, it is converted to AA by hydrolysis.

EXAMPLE 1

Test: Synthetic heparinoid material
Procedure

Mix 2.2 g AA and 22.8 g AMPS with 25.0 g $H_2O$, pull vacuum on the mixture and release to $N_2$. While stirring under a $N_2$ blanket, add:

1 ml $K_2S_2O_5$ (3.78 g/100 ml $H_2O$)
1 ml $K_2S_2O_8$ (3.76 g/100 ml $H_2O$)
1 ml $FeSO_4 7H_2O$ (0.24 g/100 ml $H_2O$)

Continue to stir, maintaining $N_2$ blanket until the mixture polymerizes. Upon polymerization, place resultant gel in a 50° C. vacuum oven overnight. After drying, remove the dried gel and place in a micro-mill and mill the gel into a powder. Dissolve 1 gram powdered gel in 100 ml saline (9 mg/ml NaCl) - making a 1% solution of AMPS/AA in DI $H_2O$.

TEST

A whole blood clotting study using canine blood was used to test the synthetic heparinoid compound of Example 1 for antithrombogenic properties.

Procedure: Whole blood clotting was done on three different samples. Whole blood clotting time, which measures the overall activity of the intrinsic clotting system, is the time required for blood to clot in a glass tube. To obtain the clotting time, the following procedure s used. First a venipuncture is performed without anticoagulant into a plastic syringe. One-milliliter aliquots of whole blood are then delivered immediately into three 12×75 mm glass tubes and a stopwatch is started as soon as the blood enters the glass tubes. Next, the tubes are placed in a water bath at 37° C. and are gently tilted every 30 seconds until a clot is seen in one of the tubes. At this time, the stopwatch is stopped and the time is recorded. The normal clotting time obtained by this method is between 4 and 8 minutes. Prolongation of the clotting time is due to marked coagulation factor deficiencies, or the presence of anticoagulants, such as heparin.

This test was carried out using - 3 drops AMPS/AA copolymer in glass test tubes, and also using; -3 drops Heparin solution in glass test tubes 1 ml of freshly drawn blood was then placed in each test tube and the time to clot was recorded.

Results

TABLE 1

| GLASS TEST TUBE | HEPARIN | | AMPS/AA addition | |
|---|---|---|---|---|
| 8 min to clot | #1 | had not clotted after 30 mins | #1 | 30 min to clot |
| 7 min to clot | #2 | had not clotted after 30 mins | #2 | 30 min to clot |
| 8 min to clot | #3 | had not clotted after 30 mins | #3 | 30 min to clot |
| 7 min to clot | #4 | had not clotted after 30 mins | #4 | 30 min to clot |

EXAMPLES 2-12

Several water soluble synthetic heparinoids were prepared according to the invention. See Table 2.

| Procedure: | 1) Copolymerize AMPS/AA in varying ratios |  |
| --- | --- | --- |
|  | 2) Test copolymer via whole blood clotting tests. |  |
| Materials: | AMPS |  |
|  | AA (inhibitor removed) |  |
|  | deionized water (DI H$_2$O) |  |
|  | K$_2$S$_2$O$_5$ |  |
|  | K$_2$S$_2$O$_8$ |  |
|  | FeSO$_4$.7H$_2$O |  |
| MW: | Acid AMPS MW 207 |  |
|  | Acrylic Acid MW 72 |  |
| Mole Ratios: | 1 mole AMPS/0 moles AA | 100% AMPS |
|  | 1 mole AMPS/1 mole AA | 50/50 AMPS AA |
|  | 3 moles AMPS/1 mole AA | 75/25 AMPS/AA |
|  | 4 moles AMPS/1 mole AA | 80/20 AMPS/AA |
|  | 9 moles AMPS/1 mole AA | 90/10 AMPS/AA |

TABLE 2/EXAMPLES 2-12

Therefore:

| AMPS/AA Mole Ratios | | Monomer Weights | | Water Weight |
|---|---|---|---|---|
| 0/100 | #2 | 0.0 g AMPS | 25.0 g AA | 25.0 g DIH$_2$O |
| 10/90 | #3 | 6.1 g AMPS | 18.9 g AA | 25.0 g DIH$_2$O |
| 20/80 | #4 | 10.5 g AMPS | 14.5 g AA | 25.0 g DIH$_2$O |
| 30/70 | #5 | 13.6 g AMPS | 11.4 g AA | 25.0 g DIH$_2$O |
| 40/60 | #6 | 16.4 g AMPS | 8.6 g AA | 25.0 g DIH$_2$O |
| 50/50 | #7 | 18.6 g AMPS | 6.4 g AA | 25.0 g DIH$_2$O |
| 60/40 | #8 | 20.3 g AMPS | 4.7 g AA | 25.0 g DIH$_2$O |
| 70/30 | #9 | 21.8 g AMPS | 3.2 g AA | 25.0 g DIH$_2$O |
| 80/20 | #10 | 23.0 g AMPS | 2.0 g AA | 25.0 g DIH$_2$ |
| 90/10 | #11 | 24.1 g AMPS | 0.9 g AA | 25.0 g DIH$_2$O |
| 100/0 | #12 | 25.0 g AMPS | 0.0 g AA | 25.0 g DIH$_2$O |

Samples of each of the above (TABLE 2) were made up and polymerized as follows:

Catalyst

| Catalyst: | | |
|---|---|---|
| 1 ml | K$_2$S$_2$O$_2$ | (0.378 g/100 ml H$_2$O) |
| 1 ml | K$_2$S$_2$O$_8$ | (0.376 g/100 ml H$_2$O) |
| 1 ml | FeSO$_4$.7H$_2$O | (0.24 g/100 ml H$_2$O) |

Procedure
1) Mix components to9ether and pull vacuum to remove O$_2$
2) Release vacuum to N$_2$ gas
3) While stirring and under a N2 blanket add catalyst
4) Continuing stirring
5) Upon polymerization place gel in vacuum oven overnight while heating
6) Remove dried gel and grind with a micro mill to a fine powder Tests Whole Blood clotting times were run on these synthetic heparinoids.

Procedure

30 μl of synthetic heparinoid solutions (100/0, 90/10, 80/20, 78/22, 70/30, 60/40, 50/50, 40,60) were placed in glass test tubes.

Also, 30 μl of phosphate buffered saline (PBS) and 30 μl (1000 u/ml) Heparin solution were placed in glass test tubes.

1 ml of freshly drawn human blood was placed in each of the test tubes.

A stop watch was started upon the addition of blood to each test tube.

The time for each blood sample to clot in each test tube was measured. The samples were performed in duplicate. 1% solutions.

TABLE 3

| | | | RESULTS: | | | | | | | |
|---|---|---|---|---|---|---|---|---|---|---|
| Glass | PBS | Heparin | 100/0 | 90/10 | 80/20 | 78/22 | 70/30 | 60/40 | 50/50 | 40/60 |
| 4 min 58 sec | 7 min 10 sec | >2 hr | >2 hr | >2 hr | 5 min 40 sec | 7 min 42 sec | 8 min 26 sec | 12 min 26 sec | 12 min 24 sec | 2 hr |
| 4 min 58 sec | 7 min 10 sec | >2 hr | >2 hr | >2 hr | 10 min 24 sec | 10 min 39 sec | 2 hr | 10 min 39 sec | >2 hr | 2 hr |

EXAMPLE 13

Procedure: CeIV ion graft AMPS/AAm in an appropriate ratio for anti-coagulant properties onto a polyurethane surface.

Then convert the AAm to AA acid by hydrolysis. Thus, producing an AMPS/AA surface having heparin - like activity. This is possible due to the enhanced hydrolytic stability of AMPS.

TABLE 4

| | Polymer Hydrolysis | |
|---|---|---|
| Polymer | Reaction Condition | % Hydrolysis |
| AMPS | 4 Hr., 5% HCl | 14% |

TABLE 4-continued

| Polymer | Polymer Hydrolysis Reaction Condition | % Hydrolysis |
|---|---|---|
| | reflux 4 Hr., 20% HCl reflux | 18% |
| Acrylamide | 1 Hr., 20% HCl reflux | 43% |
| | 4 Hr., 20% HCl reflux | 82% |

CeIV ion grafting of AMPS/Acrylamide onto Pellethane 80A (solvent extracted) films. Pellethane 80A is a Dow Chemical Company of Midland, Mich. polyurethane.

Materials
AMPS - M.W. 207
Acrylamide - M.W. 71
Make 50/50 mole ratio solution
2×2.07 g=4.14 g AMPS
2×0.71 g=1.42 g Acrylamide 40% SOLUTION BY WEIGHT: 5.56/0.4=13.9 of total weight
Need 8.34 g $H_2O$.
Procedure
1) Add 4.14 g AMPS to 1.42 g AAm
2) Add this to 8.34 g $H_2O$
3) Add CeIV ion solution. 1.7 ml/100 ml solution (~0.17 ml)
4) Degas mixture and release to $N_2$
5) Place Pellethane films (solvent extracted) into solution and let react 2 hrs.

EXAMPLE 14

Blending of APMS/AA copolymer into a polyurethane substrate.

Procedure: Mix together the following and stir the mixture until the polymers have completely dissolved.
0.8 g AMPS/AA copolymer
4.1 g Estane 42D polyurethane
120.0 g DMAC
1.0 g DI water Pour into films and dry in a 50° C. vacuum oven overnight.

The presence of sulfonic acid groups and carboxylic acid groups on the surface of the modified polyurethane was measured using toluidine blue dye. Since it is positively charged, toluidine blue dye will ionically associate with negatively charged surfaces. Therefore the binding of toluidine blue dye to the AMPA/AA surface indicates the presence of negative charges due to the sulfonic acid groups and the carboxylic acid groups on the polyurethane surface. AMPS/AA blended samples were therefore placed into a 1% toluidine blue dye/DI water solution for one minute and then rinsed in DI water. The bound dye was then released from the surface using a 1% SDS (sodium dodecyl sulfate) solution. The amount of dye eluted was determined spectrophotometrically at 640 nm. The amount of dye released from plain, untreated Estane 42D polyurethane samples and Estane 42D polyurethane samples blended with AMPS/AA copolymer is shown in FIG. 1.

As shown in FIG. 1, Estane 42D polyurethane containing no AMPS/AA copolymer adsorbed no toluidine blue dye, thereby indicating the absence of negatively charged groups. However, the AMPS/AA coating did adsorb a large amount of toluidine blue dye indicating the presence of sulfonic acid and carboxylic acid groups on the surface.

EXAMPLE 15

Dip coating of AMPS/AA copolymer onto a polyurethane substrate.

Procedure: mix together the following and stir the mixture until the AMPS/AA copolymer dissolves completely.
0.3 g AMPS/AA copolymer
50.0 g DMAC
0.3 g DI water Estane 42 D polyurethane films were dipped into the solution for 5 seconds and then removed. The films were then allowed to dry.

Figure 2:
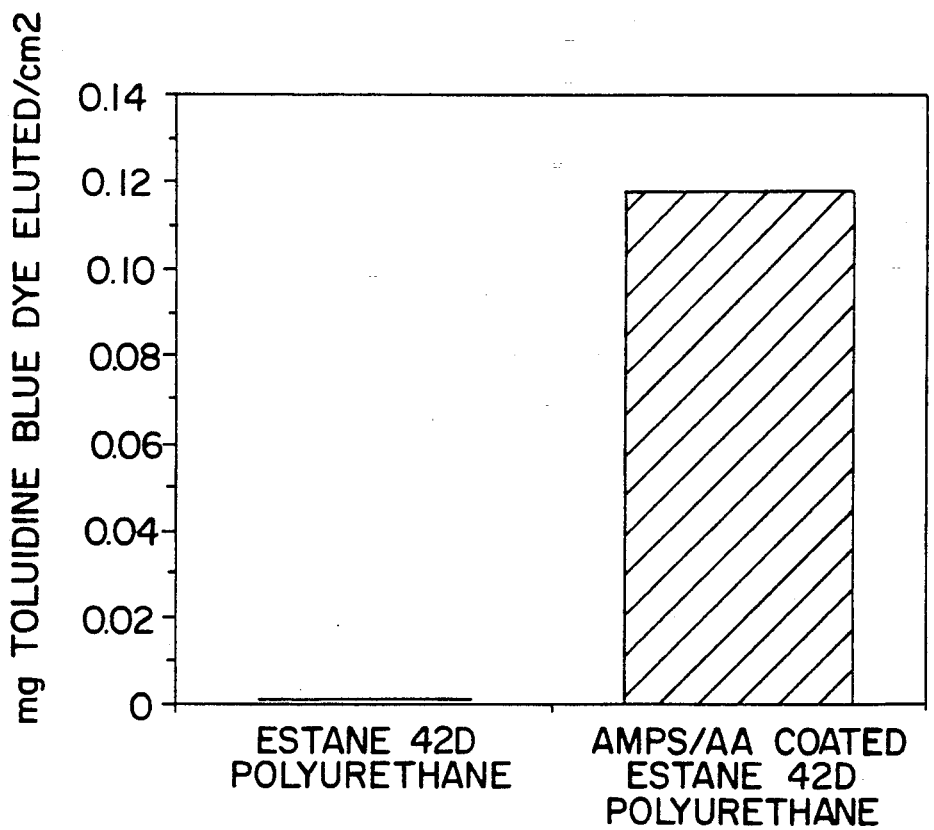
FIG. 2 is a graph comparing the presence of surface sulfonic acid groups and carboxylic acid groups for a polyurethane substrate without a dip-coated AMPS/AA copolymer with a polyurethane substrate having a dip-coated AMPS/AA copolymer.

As in Example 14, the presence of sulfonic acid and carboxylic acid groups on the surface of the modified polyurethane was measured using toluidine blue dye. A comparison of samples without and with the AMPS/AA coating respectively are shown in FIG. 2.

This completes the description of the invention. Those skilled in the art may recognize other equivalents to the specific embodiments described herein which equivalents are intended to be encompassed by the claims attached hereto.

What is claimed is:

1. A thromboresistant article for use in contact with blood or blood products, the article comprising at least one exposed surface for contacting blood or blood products, the surface having thereon an antithrombotic agent comprised of a copolymer of AA and AMPS in which the relative amounts of AA and AMPS in the copolymer are predetermined to provide $SO_3$ groups and COO— groups in a ratio comparable to the antithrombogenic binding sequence of heparin.

2. The compound of claim 1 in which the relative ratio of AA and AMPS selected is approximately 7 moles, $SO_3$— to 2 moles COO—.

3. The article of claim 1 wherein the copolymer is grafted onto the exposed surface.

4. The article of claim 1 wherein the copolymer is dip-coated onto the exposed surface.

5. The article of claim 1 wherein the exposed surface is a polymeric surface.

6. The article of claim 5 wherein the copolymer is blended with the polymeric surface.

7. The article of claim 5 wherein the polymeric surface is a polyurethane.

8. The article of claim 5 wherein the polymeric surface is a polyethylene.

9. The article of claim 5 wherein the polymeric surface is a silicone.

10. A method for providing thromboresistance to the polymeric, blood-contacting surface of an article comprising the steps of:
   (a) making an aqueous monomer solution of AAm and AMPS in a ratio to provide $SO_3$— groups and COO— groups comparable to the antithrombogenic binding sequence of heparin;
   (b) adding ceric ion to the aqueous monomer solution;
   (c) reacting the blood-contacting surface of the article with the ceric ion-containing monomer solution to produce a grafted copolymer; and
   (d) hydrolyzing the grafted copolymer to convert the AAm to AA.

11. The method of claim 10 wherein the mole ratio of AAm to AMPS is approximately 2 to 7.

12. The method of claim 10 wherein the polymeric, blood-contacting surface is a polymer selected form the group consisting of polyurethane, silicone and polyethylene.

13. A method for providing thromboresistance in a polymeric material comprising the steps of:
   (a) making an aqueous monomer solution of AA and AMPS in a ratio to provide $SO_3-$ groups and $COO-$ groups comparable to the antithrombogenic binding sequence of heparin;
   (b) polymerizing the monomer solution into a copolymer gel;
   (c) drying the copolymer gel; and
   (d) blending the dried gel with the polymeric material.

14. The method of claim 13 wherein the dried gel and polymeric material are blended by the steps of:
   (a) dissolving the dried gel and the polymeric material in a solvent;
   (b) mixing the dissolved gel and polymeric material together; and
   (c) drying the resulting mixture of dissolved gel and polymeric material.

15. The method of claim 13 wherein the mole ratio of AA to AMPS is approximately 2 to 7.

16. The method of claim 13 wherein the polymeric material is a polymer selected from the group consisting of polyurethane, silicone and polyethylene.

17. A method for providing thromboresistance to the blood-contacting surface of an article comprising the steps of:
   (a) making an aqueous monomer solution of AA and AMPS in a ratio to provide $SO_3-$ groups and $COO-$ groups comparable to the antithrombogenic binding sequence of heparin;
   (b) polymerizing the monomer solution into a copolymer gel;
   (c) drying the copolymer gel;
   (d) dissolving the dried gel in a solvent;
   (e) coating the dissolved gel onto the blood-contacting surface; and
   (f) drying the coating.

18. The method of claim 17 wherein the mole ratio of AA to AMPS is approximately 2 to 7.

* * * * *